United States Patent [19]
Lal

[11] Patent Number: 5,985,560
[45] Date of Patent: Nov. 16, 1999

[54] CLONING VECTOR AND A PROCESS FOR THE PREPARATION THEREOF

[76] Inventor: Rup Lal, Department of Zoology, University of Delhi, Delhi, 110007, India

[21] Appl. No.: 08/853,097

[22] Filed: May 8, 1997

[51] Int. Cl.⁶ .............................. C12Q 1/68; C12P 21/02; C12N 15/63; C12N 1/21

[52] U.S. Cl. ........................ 435/6; 435/69.1; 435/91.4; 435/91.41; 435/91.42; 435/252.3; 435/320.1; 435/440

[58] Field of Search .............................. 435/172.3, 320.1, 435/253.5, 91.4, 252.3, 69.1, 91.41, 91.42, 440, 6; 536/23.7

[56] References Cited

PUBLICATIONS

Lal et al. Construction of a hybrid plasmid capable of replication in Amycolatopsis mediterranei. Applied and Environmental Microbiology vol. 57 pp. 665–671, 1991.

Kumar et al. Efficient transformation of the cephamyin C producer Nocardia lactamdurans and development of shuttle and promoter–probe cloning vectors. Applied and Environmental Microbiology vol. 60 pp. 4086–4093, 1994.

Weinstock General Recombination is Escherichia coli, Chapter 60 in Escherichia coli and Salmonella typhimurium, Neidhardt Ed, Amer. Soc. for Microbiology, Washington D.C., 1987.

*Primary Examiner*—David Guzo
*Assistant Examiner*—John S. Brusca
*Attorney, Agent, or Firm*—Venable; George H. Spencer; Charles C. P. Rories

[57] ABSTRACT

This invention relates to a method for the preparation of a series of cloning vectors and such cloning vectors prepared therefrom. The method consists in the step of digestion of pRL1 derivative with a restriction enzyme BamHI and digesting the pIJ4026 by BglII and electroeluting the ermE gene. The linear DNA having pRL1 derivative is ligated with ermE gene and then transformed into *E. coli* GM2163. The transformants are screened for the presence of concatamers and that concatamers of pRL50 and pRL80 DNAs being isolated from *E. coli*. The transformants are selected under appropriate antibiotic selection pressure.

19 Claims, 18 Drawing Sheets

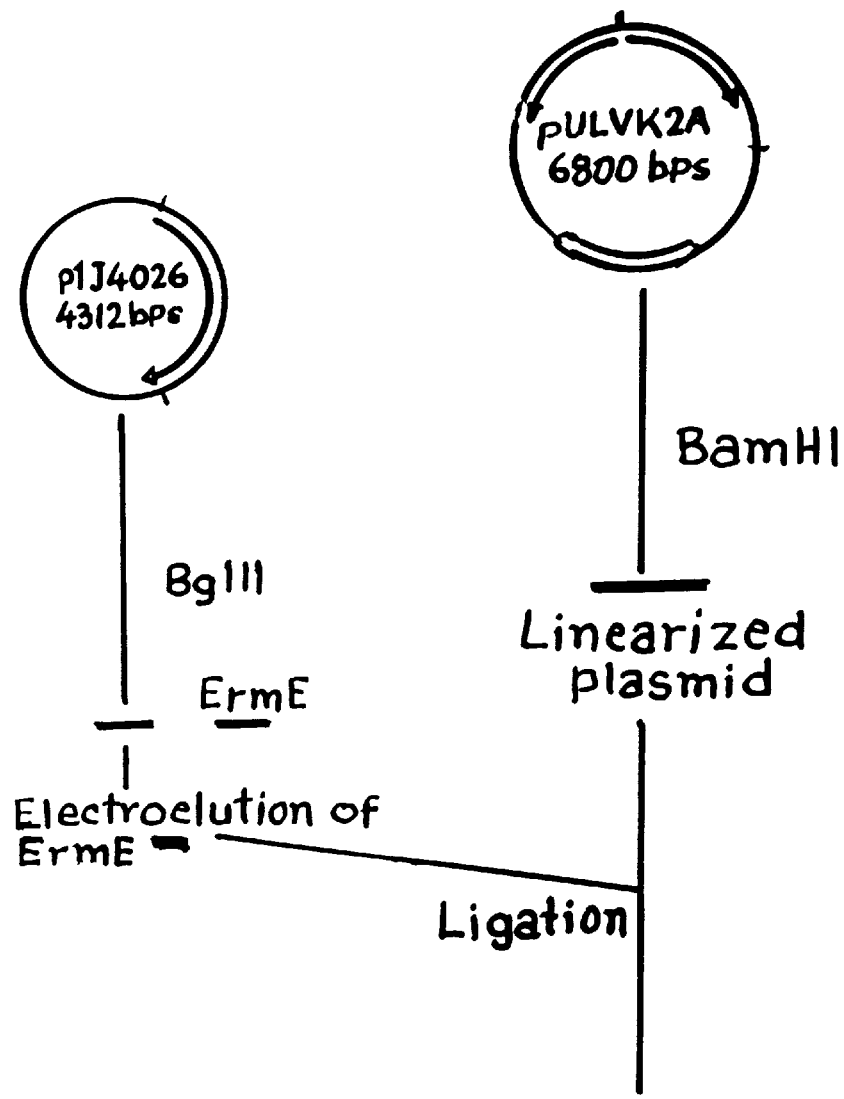
FIG. 2C
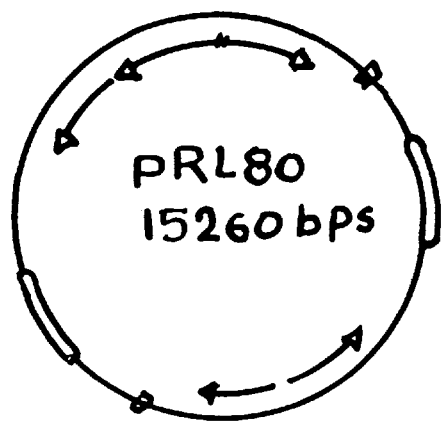

FIG. 2D
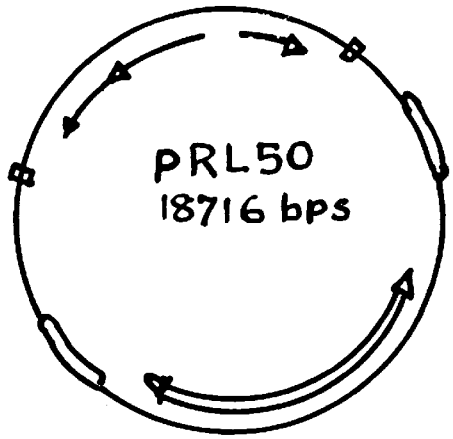
Transformation in *Amycolatopsis mediterranei* by electroporation
Selection
On erythromycin | Spontaneous deletion and intramolecular recombination | on neomycin
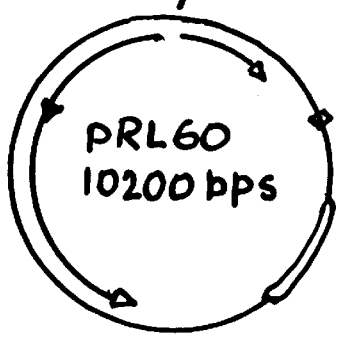  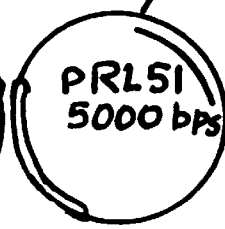 
Transformation in *Amycolatopsis* by electroporation

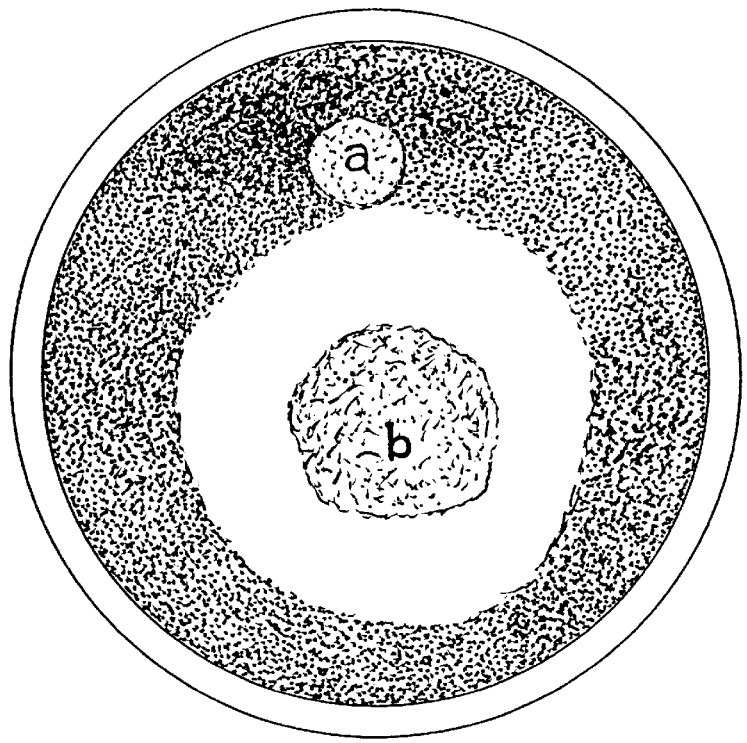

Use of α-amylase gene of *Streptomyces griseus* for the selection of transformants in *Amycolatopsis mediterranei* a - *A. mediterranei* harboring pRLM20 (without α-amylase gene)

b - *A. mediterranei* harboring pRL60 (due to α-amylase activity, a halo appears by the side of transformant containing pRL60 that carries α-amylase gene as marker) on nutrient medium containing 1% starch after iodine staining.

FIG. 14

CLONING VECTOR AND A PROCESS FOR THE PREPARATION THEREOF

FIELD OF THE INVENTION

This invention relates to a series of cloning vectors and a process for the preparation of said series of cloning vectors, selection of several effective cloning vectors with suitable selectable marker genes, an efficient method of transformation through electroporation, and the application of these cloning vectors in genetic manipulations of A. mediterranei.

BACKGROUND OF THE INVENTION

It is known that several species and strains of the genus Amycolatopsis synthesize compounds which are produced on an industrial scale. They make a variety of extracellular enzymes such as amylases, cellulases and proteases as well as secondary metabolites such as antibiotics and other pharmacologically active molecules. As a result, there has been an increasing interest in developing gene cloning methods for these organisms.

A. mediterranei and A. orientalis are known to produce rifamycins (Margalith and Pagani Appl. Microbiol 9:325–334, 1961) and vancomycins (Barna and Williams, Annu. Rev. Microbiol. 38:339–357, 1984) respectively. A recently introduced glycopeptide antibiotic Balhimycin which exhibits antibacterial activity against methicillin resistant Staphylococcus aureus strains has been isolated from Amycolatopsis sp. Y-86 21022DSM 5908 (Nadkarni et al. Antibiotics 47:334–341 1994). In addition, species of Amycolatopsis alongwith other closely related genera of the order Actinomycetales form the third major group of bacteria in terms of scales of antibiotic production.

Methods of gene cloning have been developed for several species of Streptomyces (Khosla et al. Molecular Microbiol. 6:3237–3239, 1992; Lal et al. CRC Critical Rev. Microbiol. 22 220–1257, 1996; Hopwood et al. Laboratory Manual, John Innes Foundation Norwich, 1985). Although A. mediterranei belongs to the same order (Actinomycetales) to which Streptomyces belongs, recombinant DNA techniques were not available for Amycolatopsis until recently. This was mainly due to the lack of any plasmid, suitable for vector development in Amycolatopsis. Furthermore, standard transformation procedures as used in Streptomyces. spp. are not applicable to these organisms and conjugation was the only technique for the introduction of DNA into these organisms (Schupp et al. J. Bacteriol. 121:128–136, 1975).

Several scientific groups have attempted to develop suitable cloning vectors for these organisms (Madon et al. Mol. Genet. 209:257–264 1987; Moretti et al. Plasmid 1:126–133 1985; Schupp and Divers, FEMS Microbiol. Lett. 36:159–162, 1986; Lal et al. CRC Critical Rev. Microbiol. 21:19–30, 1995) but this did not meet with any success. For instance, an indigenous plasmid pMEA100 (27.7 kb) was isolated from A. mediterranei LBG A3136 which could not be developed into a suitable cloning vector as it integrates into the chromosome (Zhu et al. Plasmid, 24:132–142, 1990). Although conjugative plasmid pMEA300 was subsequently isolated from A. methanolica NCIB 11946 (Vrijbloed et al. J. Bacteriol. 176:7086–7090, 1994; Vrijbloed et al. J. Bacteriol. 177:6666–6669, 1995) this plasmid also could not be suitably modified into a versatile cloning vector as it occurred both in the free and integrated states. For these reasons studies on genetic manipulations of A. mediterranei and related species remained hampered for quite sometime. We succeeded in the development of a preliminary cloning vector pRL1 (10.4 kb) for A. mediterranei (Lal et al. Appl. Environ. Microbiol. 57:665–671, 1991). The preliminary cloning vector pRL1 was constructed by cloning a 5.1 kb fragment of pA387 (29.6 kb), an indigenous plasmid of A. orientalis DSM 43387 into E. coli vector pDM10. pRL1 could be transformed into A. mediterranei and A. orientalis only by electroporation.

A disadvantage, inspite of the preliminary success in developing cloning vector pRL1 was that this vector required further improvements in terms of reduction in its size (pRL1 has a size of 10.4 kb). A further disadvantage was that the vector needed the addition of suitable selectable marker genes (which could be suitably expressed in different species and strains of Amycolatopsis) to make it an ideal cloning vector. In fact this was a very serious bottleneck in development of cloning vector for Amycolatopsis as many selectable marker genes have not yet become available for this group of organisms. Commonly available antibiotic resistance markers such as thiostrepton, hyromycin, viomycin, gentamycin etc. are not expressed suitably in Amycolatopsis, thus making them unsuitable for use. Not only this, even the kanamycin or neomycin resistance gene (km/neo) of pRL1 which functions effectively in E. coli was found not to be very suitable for selection of transformants in Amycolatopsis since different species or strains of Amycolatopsis were intrinsically resistant to kanamycin/neomycin. When transformants were selected under neomycin pressure, several mutant colonies appeared among transformants.

Another disadvantage was that the method of transformation through electroporation which we had developed in 1991 (Lal et al. Appl. Environ. Microbiol. 57,665–671, 1991) did not give transformation efficiency as high as required for a vector to be used for gene cloning. However, Kumar et al. (1994) (Kumar et al. Appl. Environ. Microbiol 60:4086–4093, 1994) used pRL1 cloning vector developed by us (Lal et al. Appl. Environ. Microbiol. 57:665–671, 1991) or derivatives derived from pRL1 to transform Nocardia lactamdurans (cephamycin producer) and reported an efficient method of transformation (based on the treatment of filaments with $MgCl_2$ and CsCl as developed by Madon and Hutter (1991) (Madon and Hutter, J. Bacteriol. 173:6325–6331, 1991). In this method they transformed N. lactamdurans by direct treatment of mycelia with polyethylene glycol 1000 and CsCl. However, this method also did not work when tried in several strains of A. mediterranei and A. orientalis. Moreover the above method as reported by Kumar et al. (1994) is very cumbersome and time consuming.

Although Kumar et al. 1994 (Appl. Environ. Microbiol. 60 4086–4093 1994) also succeeded in introducing two markers: α-amylase genes of Streptomyces griseus and apramycin resistance gene of Streptomyces griesofuscus in pRL1 derivatives, these vectors again could not be used in A. mediterranei and A. orientalis for cloning as they lacked several features generally found in an ideal cloning vector.

OBJECTS OF THE INVENTION

An object of this invention is to propose a series of new cloning vectors capable of having various advantageous applications.

Another object of this invention is to propose a process for the preparation of effective cloning vectors avoiding the steps of in vitro gene manipulations.

Yet another object is to propose an efficient method of transformation through electroporation.

Still another object is to propose a process for the preparation of effective cloning vectors which avoids the major disadvantages associated in the known development of gene cloning methods for A. mediterranei.

SUMMARY OF THE INVENTION

This invention relates to a novel process for the development of cloning vectors (which can be used as model for the development of cloning vectors for other groups of microorganisms) but also the development of an effective series of cloning vectors with suitable markers genes and method of electroporation for the efficient transformation of the different species and strains of A. mediterranei. The process comprises pRL1 derivatives containing α-amy or am and km/neo genes and digesting both with the vectors with restriction enzymes. Another cloning vector pIJ4026 which contains ermE is also digested and ermE insert electroeluted. The ermE gene is ligated separately with each linear plasmid and ligation mix transformed into E. coli GM2163. Clones containing unstable plasmids with one additional copy of the vector and ermE insert (concatamers pRL50 and pRL80) among recombinant clones in E. coli are then selected and plasmid DNAs of the large sized unstable vectors (which are concatamers and contain ermE insert) are transferred into A. mediterranei. Transformation is finally confirmed by isolating plasmid DNA from the transformants. The transformants are selected under different antibiotic pressure. Accordingly, the concatamer pRL50 and pRL80 undergo homologous or intramolecular recombination and spontaneous deletions in A. mediterranei. The type and the size of the deletion are dependent on the type of antibiotic used as pressure. When erythromycin is used as selection pressure a fragment of 8.5 kb is spontaneously deleted from pRL50 resulting in the formation of plasmid pRL60 (10.2 kb) with the exception of pRL53 (7.2 kb) which resulted from a deletion of 11.5 kb from pRL50. When selected under neomycin pressure a large fragment of 13.7 kb was deleted from pRL50 resulting in the formation of pRL51 (5.0 kb). Thus by simply changing the selection pressure the desired deletions and recombinations can be created. Using the method of invention the first series of effective cloning vector have been developed for different strains of A. mediterranei. In contrast cloning vector pRLM10 is however, developed simply by deleting 3.4 kb DNA fragment from pRL1 through in vitro DNA manipulations. It has a size of 7.4 kb, contains km/neo as marker and can be transformed in A. mediterranei and A. orientalis (vancomycin producer) and E. coli. Cloning vectors pRLM20 and pRLM30 (12.1 kb) have also been developed by cloning ermE into pRL1 through in vitro gene manipulations. These vectors can be suitably transformed in different strains and species of Amycolatopsis through electroporation. pRL50 a concatamer has a size of 18.7 kb contains in addition to ermE, two copies each of km/neo and α-amy genes. When transformed in A. mediterranei and selected under erythromycin pressure, it always releases a fragment of 8.5 kb resulting in the formation of pRL60. pRL60 becomes an ideal cloning vector of the series derived from pRL1. pRL60 has a size of 10.2 kb and contains two origins of replication (one derived from pA387:pA-rep and other from pBR322:pBR-ori), and three marker genes: km/neo, ermE and α-amy. The first marker gene functions effectively in E. coli and the remaining two markers in different species and strains of Amycolatopsis. The development of cloning vector with amylase gene and its successful expression in A. mediterranei made it possible to select transformants and recombinants directly. Similarly another concatamer pRL80 has a size of 15.3 kb and contains in addition to ermE, two copies each of km/neo and am genes and an additional copy of the vector. pRL80 when transformed in A. mediterranei and selected under apramycin resulted in the formation of pRL81 and pRL82. pRL81 also contains three marker genes km/neo, ermE and am whereas pRL82 contains only two marker genes: km/neo and am. Apramycin resistance gene was also found to be a good selectable marker for A. mediterranei. The cloning of suitable marker genes led to the development and optimization of transformation protocol through electroporation for different strains of A. mediterranei. By using optimum conditions a transformation efficiency of $1 \times 10^5$ transformants/μg of DNA can be obtained. All these cloning vectors can be transformed through electroporation in different strains of A. mediterranei which produce a variety of rifamycins. These strains include A. mediterranei DSM 40773 (rifamycin B); A. mediterranei 43304 (rifamycin B); A. mediterranei 46095 (rifamycin SV); A. mediterranei 46096 (rifamycin derivatives); A. mediterranei MTCC 14 (Rifamycin B) and A. mediterranei MTCC 17 (rifamycin SV). These cloning vectors could also be transformed into mutant strains derived from an industrial strain of A. mediterranei N813 of Ciba Geigy (Switzerland). These mutants strains are: A. mediterranei W-2800 ans-12 (rifamycin W); A. mediterranei T-208 ans-11 pur-20 (rifamycin W and prine auxotroph); A. mediterranei T-206 ans-13, leu-1 str-2 (protorifamycins leucine auxotroph), streptomycin resistance); A. mediterranei F1/24 ans-13 (protorifamycin); A. mediterranei T-195, ans-13, thi-8 (protorifamycin thiamine auxotroph); A. mediterranei S2802 ans-4, his-3 (rifa S, histidine auxotroph) and A. mediterranei S2804 ans-4 ser-5 (rifa S, serine auxotroph). pRL-vectors could also be transformed in vancomycin producer A. orientalis DSM 40040.

BRIEF DESCRIPTION OF THE DRAWINGS

FIG. 14 shows the detection of α-amylase activity *A. mediterranei*: The transformants containing pRLM20 (A) and pRL60 (B) were grown on YM medium+1% starch and after 4–5 days of growth, the plates were sprayed with iodine to detect α-amylase activity. Halo around transformant B indicate α-amylase activity due to the expression of α-amy gene. This method is very convenient to select the transformation or recombinant directly.

DETAILED DESCRIPTION OF THE INVENTION

The salient features of pRL series are:

1. Plasmid size ranges from 5 kb to 18.7 kb;
2. Each cloning vector has two origins of replication-pBR-ori, pA-rep;
3. Each cloning vector has any of the combination of the following markers: α-amylase, ermE, km and amp;
4. A wide range of markers including α-amy, ermE and am function effectively in *A. mediterranei* and related strains;
5. α-amylase can now be used as morphological marker for the selection of transformants;
6. Cloning in α-amylase gene can now lead to the direct selection of recombinant clones after iodine staining in *Amycolatopsis mediterranei;*
7. The plasmids have broad host range as they are functional in almost all the species of Amycolatopsis so far tested (Table 1);
8. This is the first effective series of cloning vectors developed for different strains of *A. mediterranei.*

Figure 3:
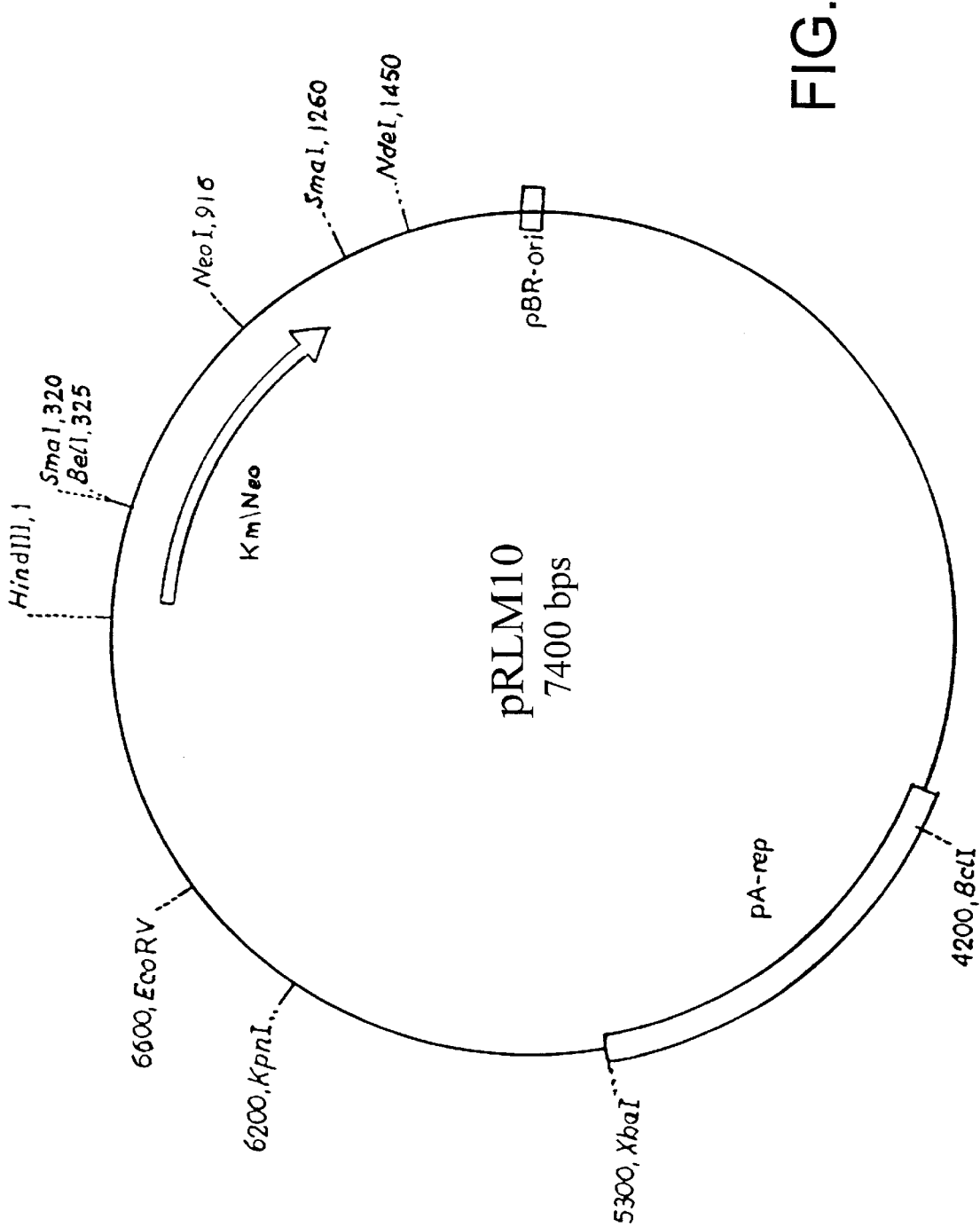
FIG. 3 shows the restriction map of cloning vector pRLM10. This vector was generated by exonuclease deletions of pRL1 and has only one marker gene: km/neo.
Figure 4:
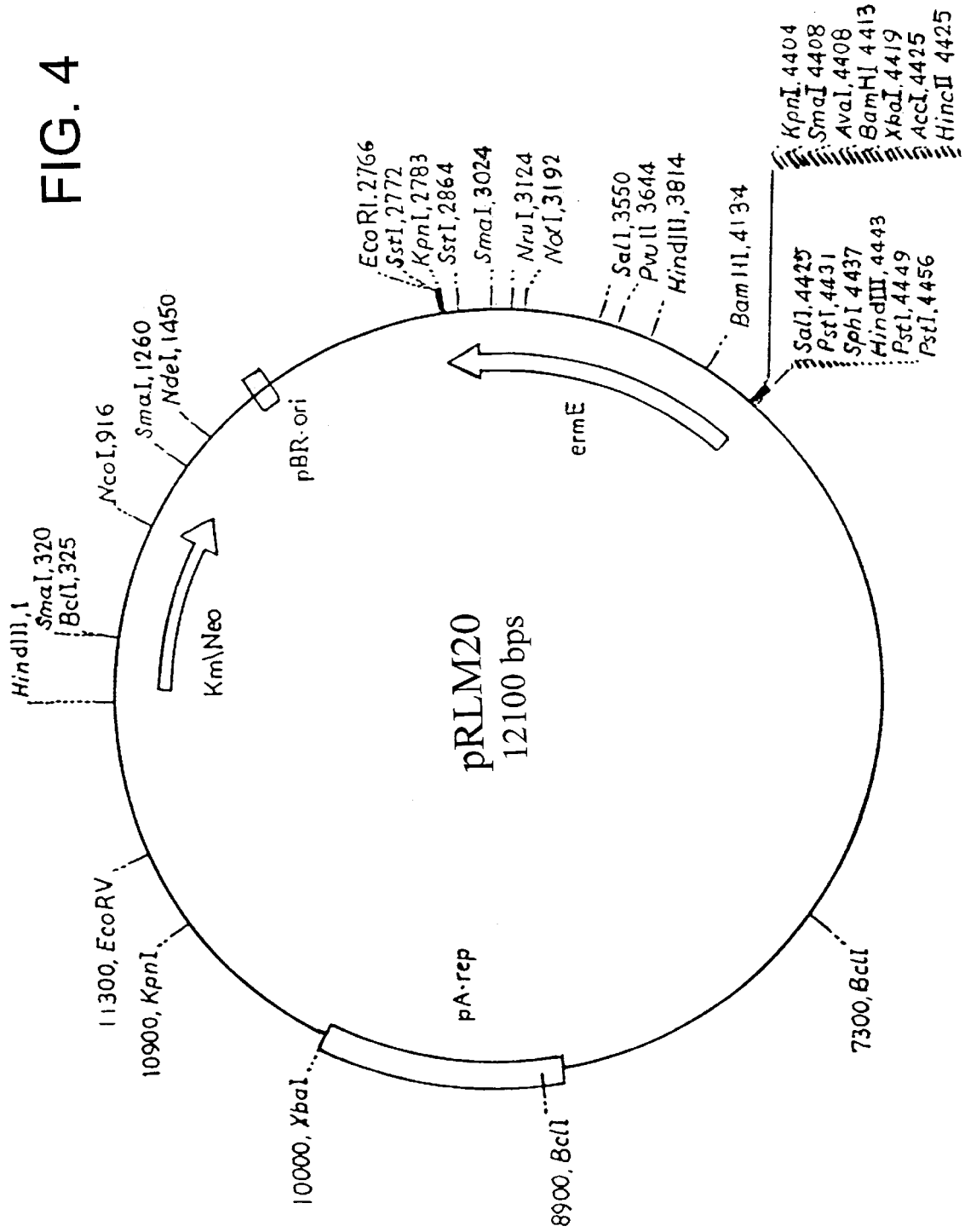
FIG. 4 shows the restriction map of cloning vector pRLM20. ermE gene as a marker was cloned in anticlockwise direction in BamH1 site of pRL1.
Figure 5:
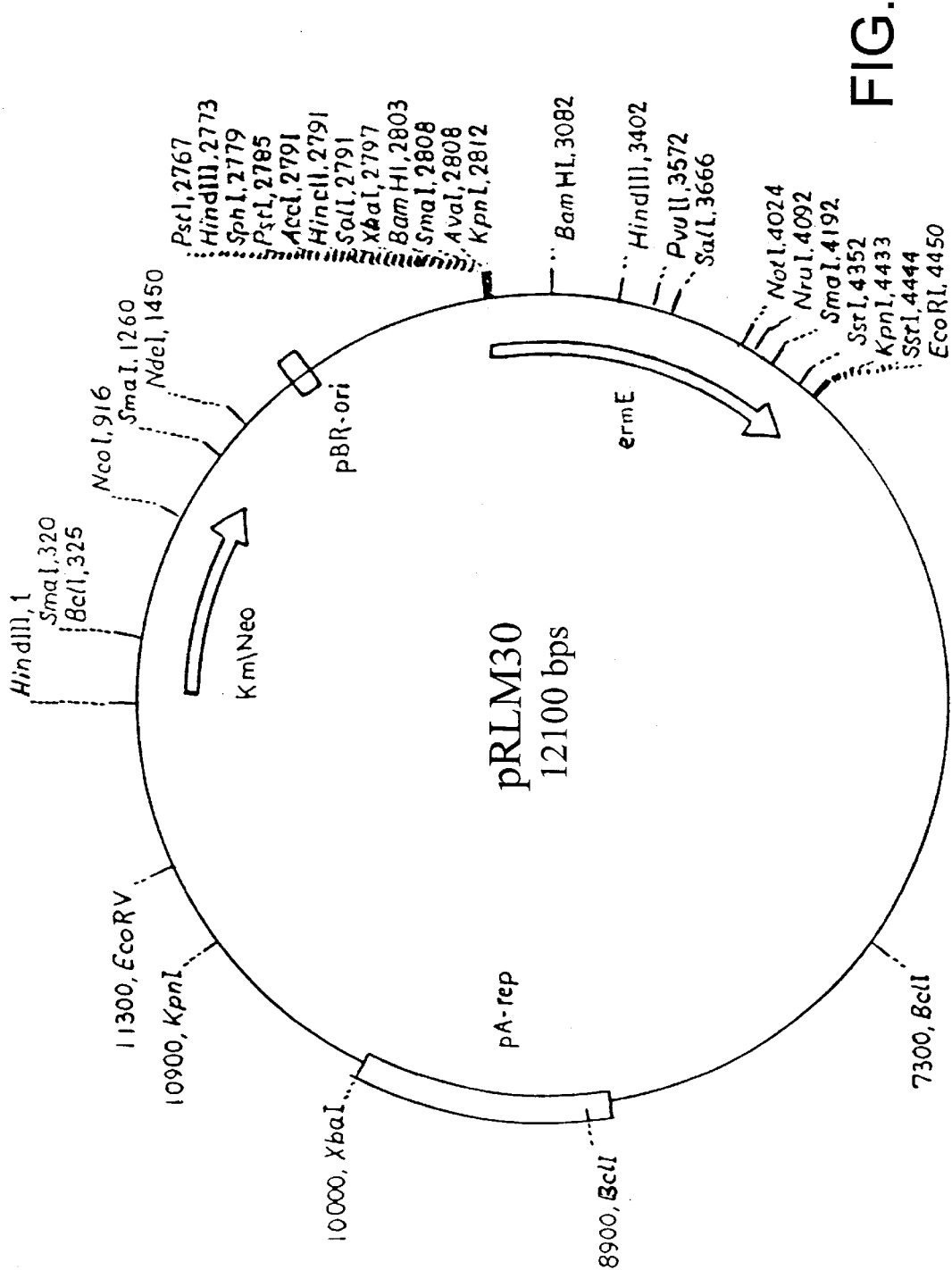
FIG. 5 shows the restriction map of cloning vector pRLM30. ermE gene as a marker was cloned in clockwise direction in BamH1 site of pRL1.

The present method resides in first developing a large unstable plasmid usually concatamer with effective marker such as erythromycin resistance gene (ermE) in *E. coli* and then transform it into Amycolatopsis, virtually forcing the plasmid to undergo intramolecular recombinations and substantial deletions of extra DNA. This finally results in the development of smaller but stable and more effective vector with several characteristic features. This method thus eliminates the more cumbersome and expensive method of reducing the size by using nested deletions or in vitro manipulations of DNA. For instance, pRLM10 (FIG. 3) is generated by simple deletions by using exonucleases and pRLM20 (FIG. 4) and pRLM30 (FIG. 5) constructed by cloning ermE of pIJ4026 (provided by M. J. Bibb, John Innes Institute, Norwich). But these methods never proved much effective and economical. The only inference which could be drawn by cloning ermE in pRL1 directly was that ermE is expressed equally well in the background of *A. mediterranei* and *A. orientalis* (as all the transformants analyzed showed the presence of plasmids and none of them was mutant). However, this further increased the size of cloning vectors from 10.4 kb (pRL1) to 12.1 kb (pRLM20, pRLM30). Instead of resorting to further in vitro DNA manipulations, the process of the present invention simultaneously takes care of generating substantial deletions thus removing the extra portion of DNA through intramolecular recombinations and retaining essential selectable markers in the final vectors which are effectively expressed in several strains of *A. mediterranei* and related species.

Figure 6:
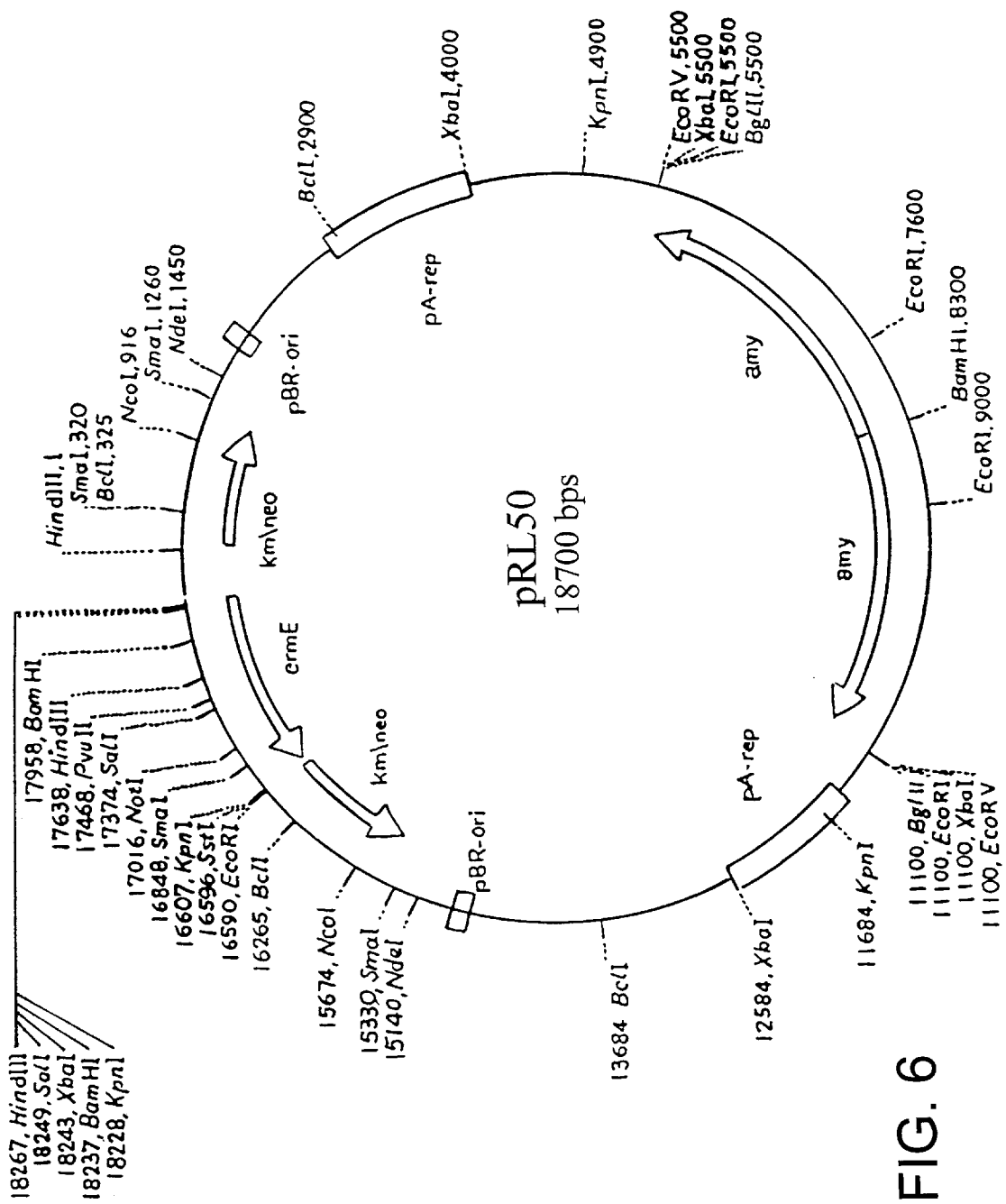
FIG. 6 shows the restriction map of cloning vector pRL50. pRL50 is concatamer or unstable plasmid constructed by cloning ermE gene in BamH1 site of pRL1 derivative pULAM2 and selected in E. coli. It contains two copies of each km/neo, an additional copy of pULAM2 and one copy of ermE. This plasmid when transformed in A. mediterranei and transformants selected under antibiotic selection pressure resulted in the formation of plasmid pRL51, pRL53 and pRL60.
Figure 7:
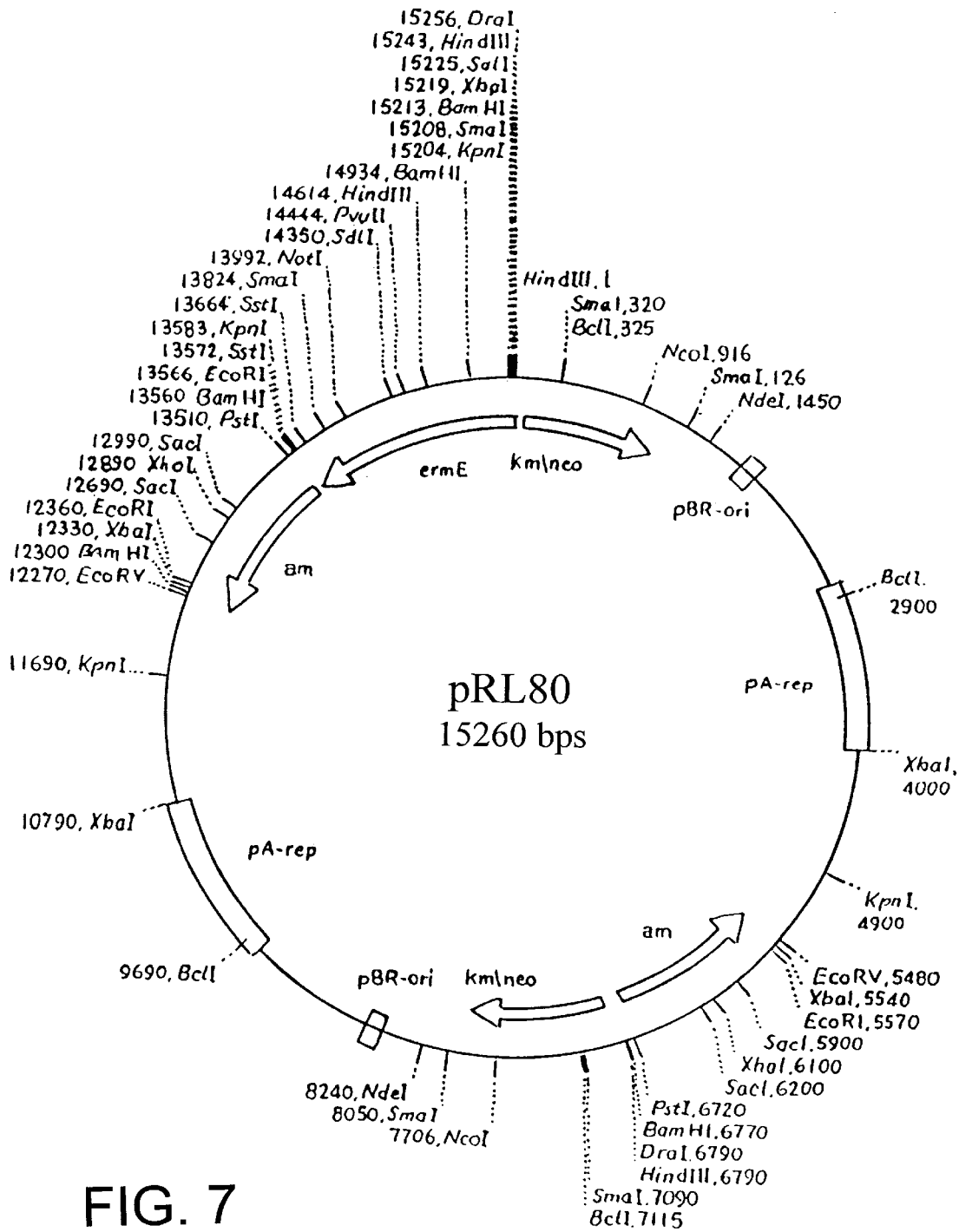
FIG. 7 shows restriction map of concatamer pRL80 (15.2 kb) containing two copies of km/neo and am genes, an additional copy of plasmid pULVK2A, and one copy of an ermE gene.
Figure 8:
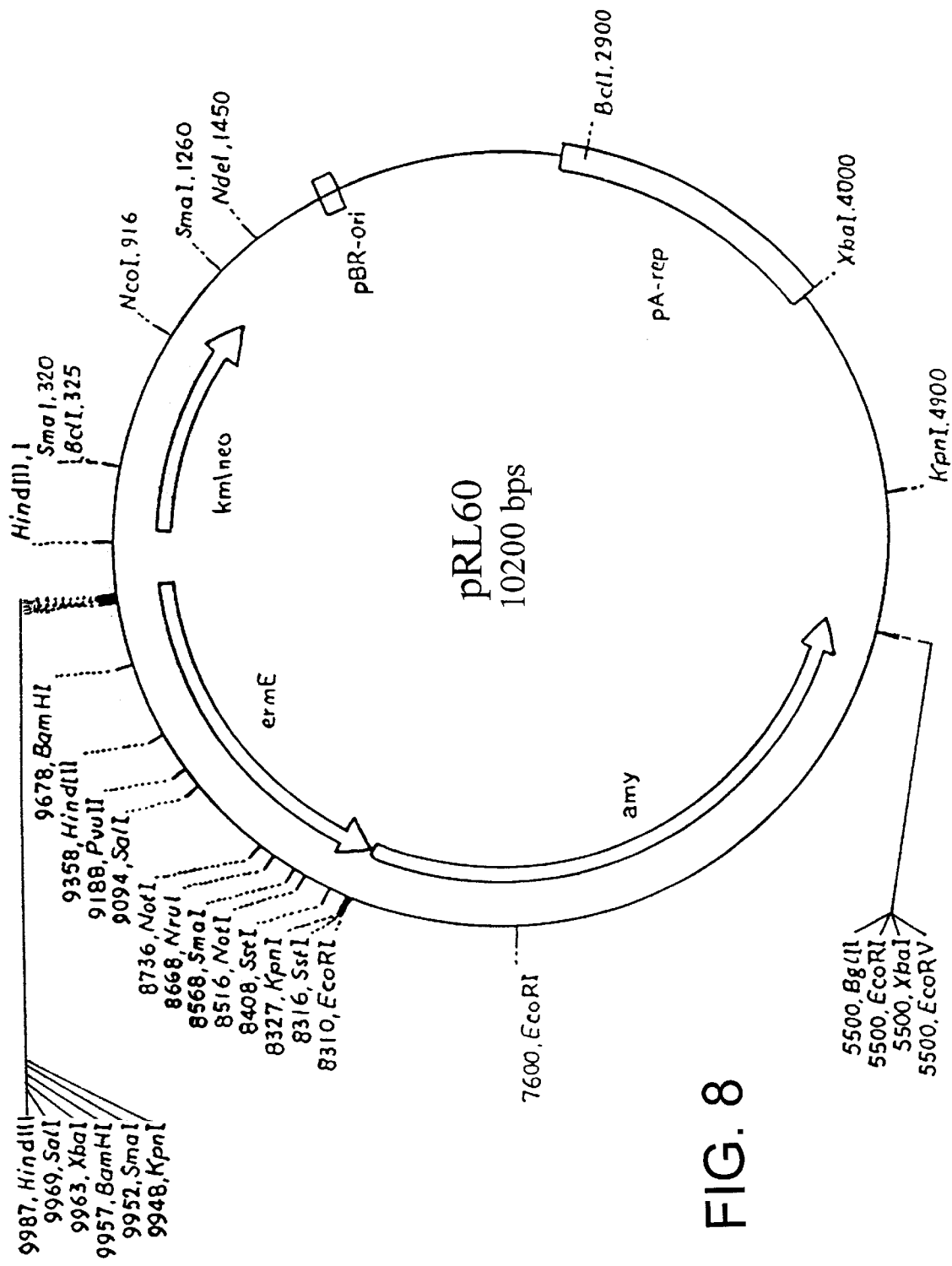
FIG. 8 shows the restriction map of pRL60, an ideal cloning vector of the series formed by spontaneous deletion of 8.5 kb fragment from pRL50 and contains km/neo, α-amy and ermE.
Figure 9:
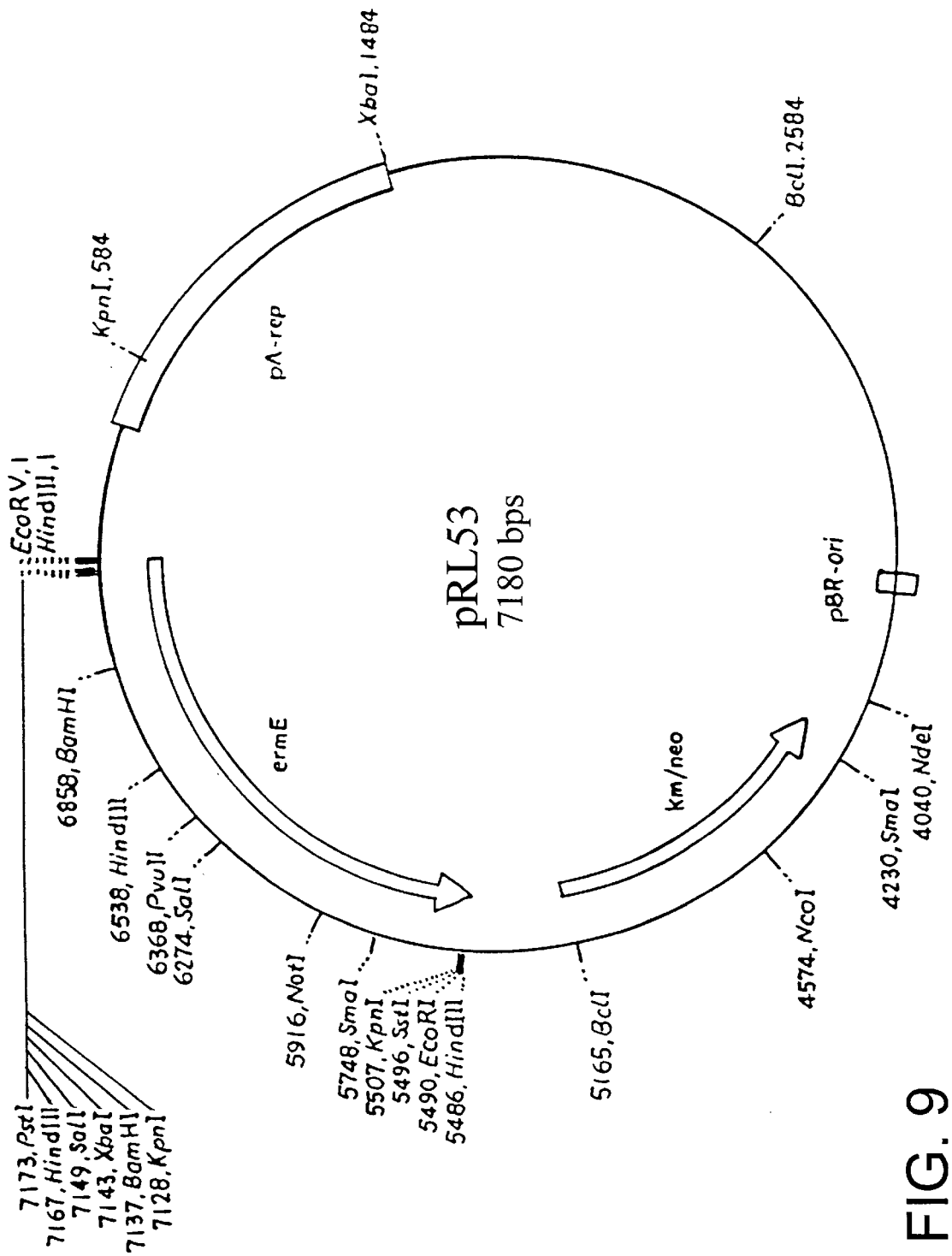
FIG. 9 shows the restriction map of cloning vector pRL53. This vector contains km/neo and ermE as the selectable marker genes and was formed when pRL50 was transformed into *A. mediterranei* and transformants selected under erythromycin pressure.
Figure 10:
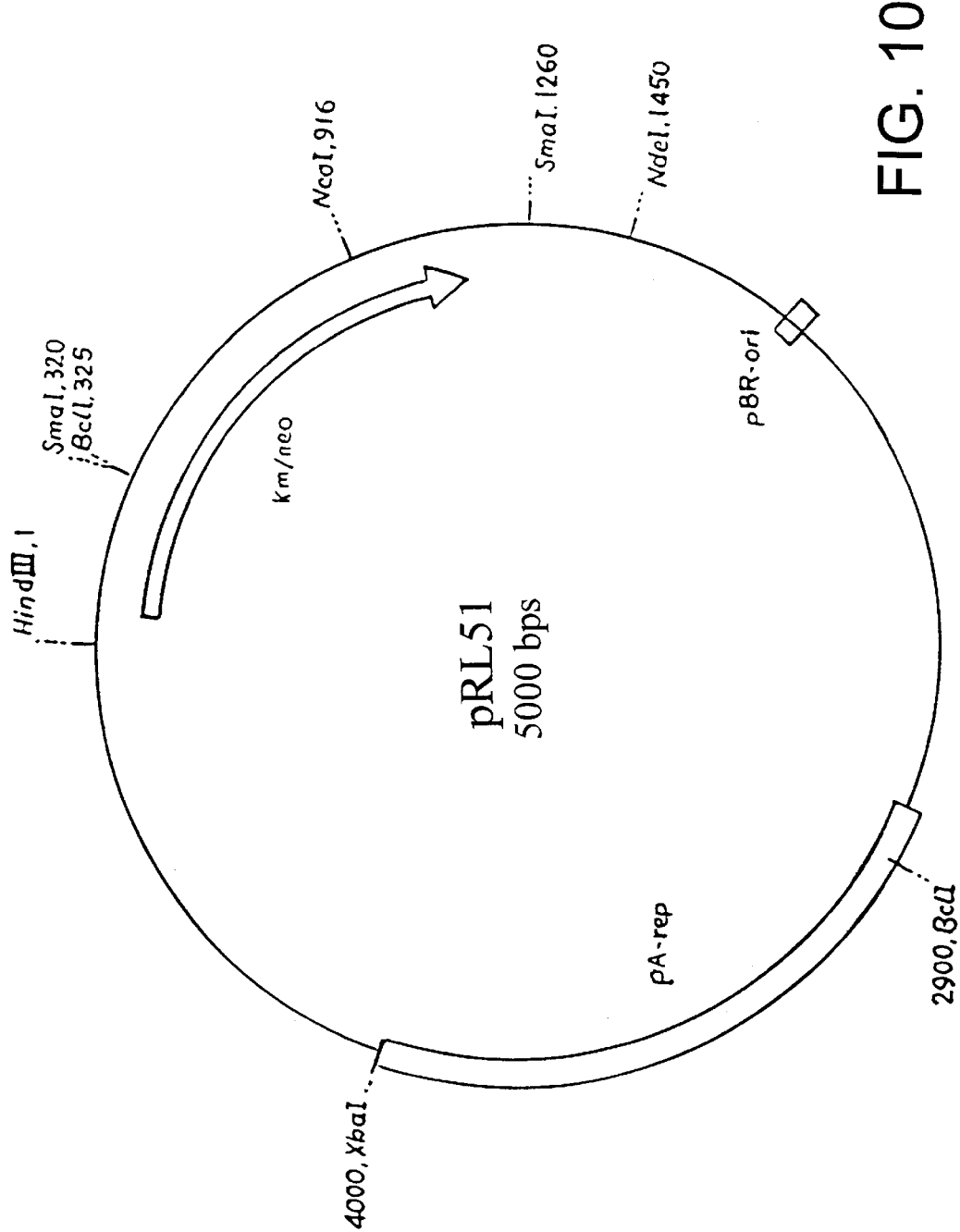
FIG. 10 shows the restriction map of cloning vector pRL51. This cloning vector has minimum pA-rep replicon, and only one marker gene km/neo and a minimum size 5 kb. This plasmid was formed when pRL50 was transformed into *A. mediterranei* and transformants selected under neomycin pressure.
Figure 11:
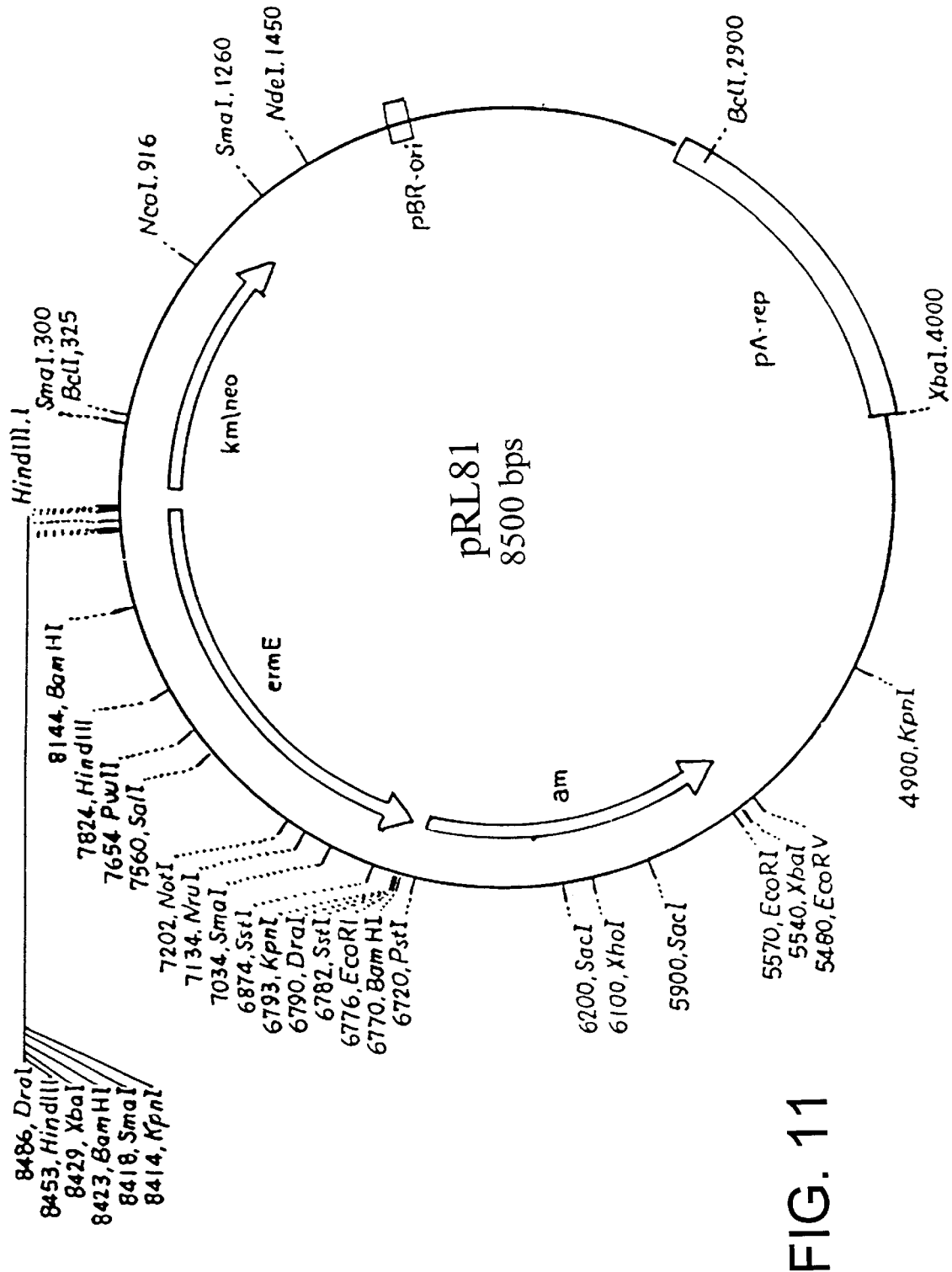
FIG. 11 shows restriction map of plasmid pRL81 (8.5 kb) formed by spontaneus deletion of 6.8 kb from pRL80 and contains am, km/neo and ermE genes as selectable markers.
Figure 12:
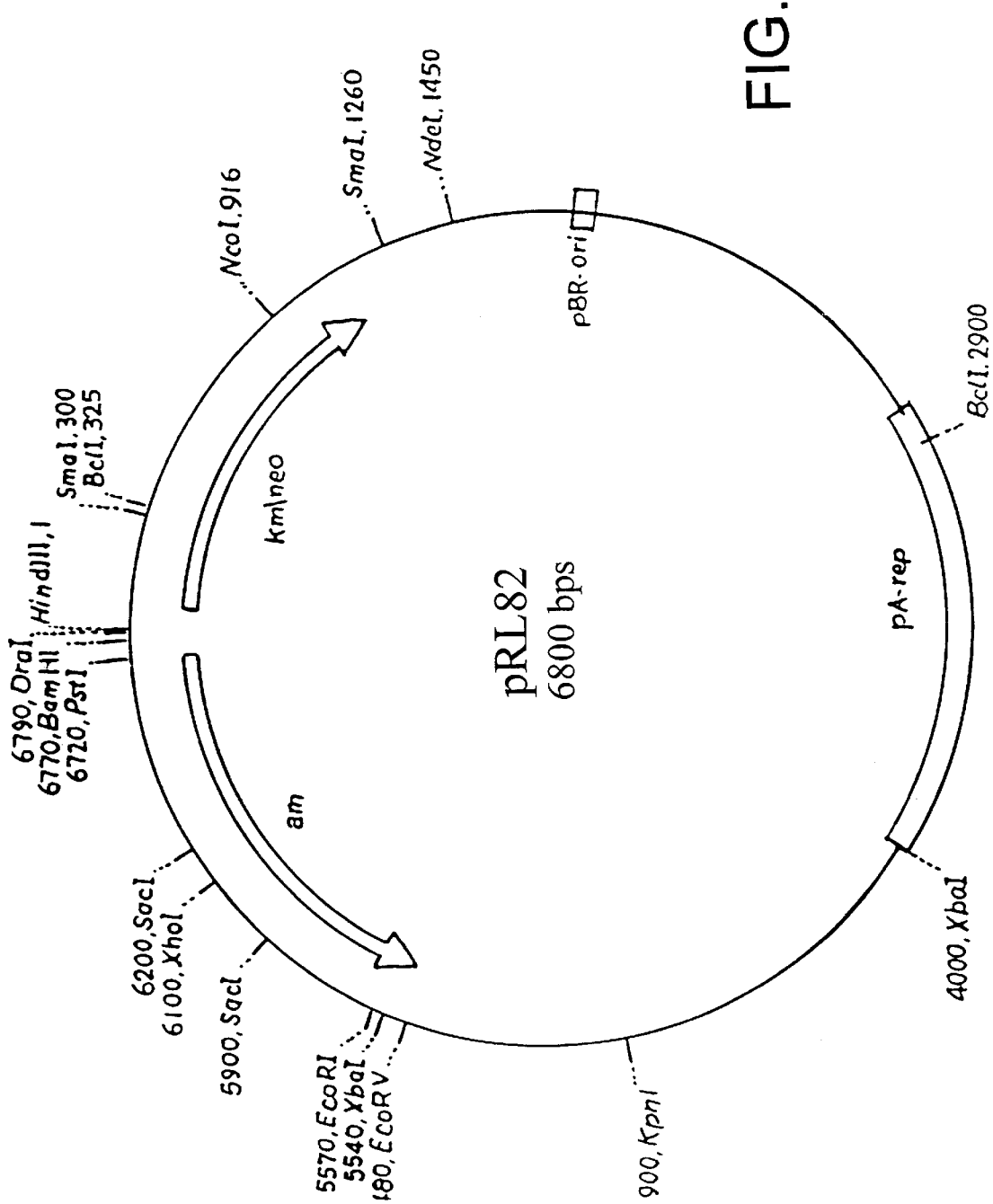
FIG. 12 shows restriction map of plasmid pRL82 (6.8 kb) formed by spontaneous deletion of 8.5 kb from pRL80 and contains am, and km/neo as selectable marker genes.

In this method an additional marker gene such as ermE of *Saccharopolyspora erythraea* in pIJ4026 along with an additional copy of the vector is cloned. For instance while cloning ermE in pULAM2 or pULVK2A which are derivatives of pRL1, an additional copy of the vector is introduced and ligation mix first transformed into *E. coli*. Recombinant plasmids generally concatamers that contain ermE insert are selected in *E. coli* through colony hybridization by using ermE as the probe. In the above cases two plasmid concatamers pRL50 (18.7 kb FIG. 6) and pRL80 (15.3 kb FIG. 7) are thus generated. pRL50 for instance is a concatamer containing two copies each of -amy, km/neo, a single copy of ermE and an additional copy of pULAM2. Similarly pRL80 contains two copies each of km/neo, am one copy of ermE and an additional copy of pULVK2A. Transformation of *A. mediterranei* with pRL50 and pRL80 DNAs isolated from *E. coli* GM2163 through electroporation and selection of transformants under different antibiotic pressure such as erythromycin, neomycin and apramycin always leads to intramolecular (intraplasmid) recombinations, retaining only those portions of the plasmid which are essential for their maintenance and propagation of the plasmids in. *A. mediterranei* DSM 40773 through electroporation and transformants selected on erythromycin pressure there was a deletion of 8.5 kb in pRL50 resulting in formation of plasmid pRL60 (10.2 kb FIG. 8). pRL60 has a size of 10.2 kb and three selectable marker genes: α-amy, ermE and km/neo. However, in an exceptional case one clone is found to contain a plasmid pRL53 (7.2 kb, FIG. 9) which is formed by a deletion of 11.5 kb in pRL50. This cloning vector had only km/neo and ermE marker genes. On the contrary, when transformants were selected under neomycin selection pressure a deletion of 13.7 kb in pRL50 occurred resulting in the formation of plasmid pRL51 (5.0 kb) (FIG. 10) which also lacked α-amy gene and hence α-amylase activity. Plasmid pRL51 which is quite stable, has a size of 5.0 kb and contains only km/neo as the marker. Similarly second concatamer pRL80 (FIG. 7) when transformed into *A. mediterranei* and transformants selected under apramycin pressure showed two types of transformants. The cloning vectors isolated from these transformants were named as pRL81 and pRL82. pRL81 is of 8.5 kb size and containing am, km/neo and ermE as the selectable markers (FIG. 11) whereas pRL82 is 6.8 kb and contains only am and km/neo genes as selectable markers (FIG. 12). Thus antibiotic pressure can be used as a switch which can instigate A. mediterranei to generate the required intramolecular plasmid recombinations. This method can be strategically utilized to reduce the size of plasmid cloning vectors through deletions and intraplasmid recombinations eliminating the need for using a tedious, more expensive and cumbersome process of creating deletions in vitro by restriction enzymes and exonucleases.

Figure 13:
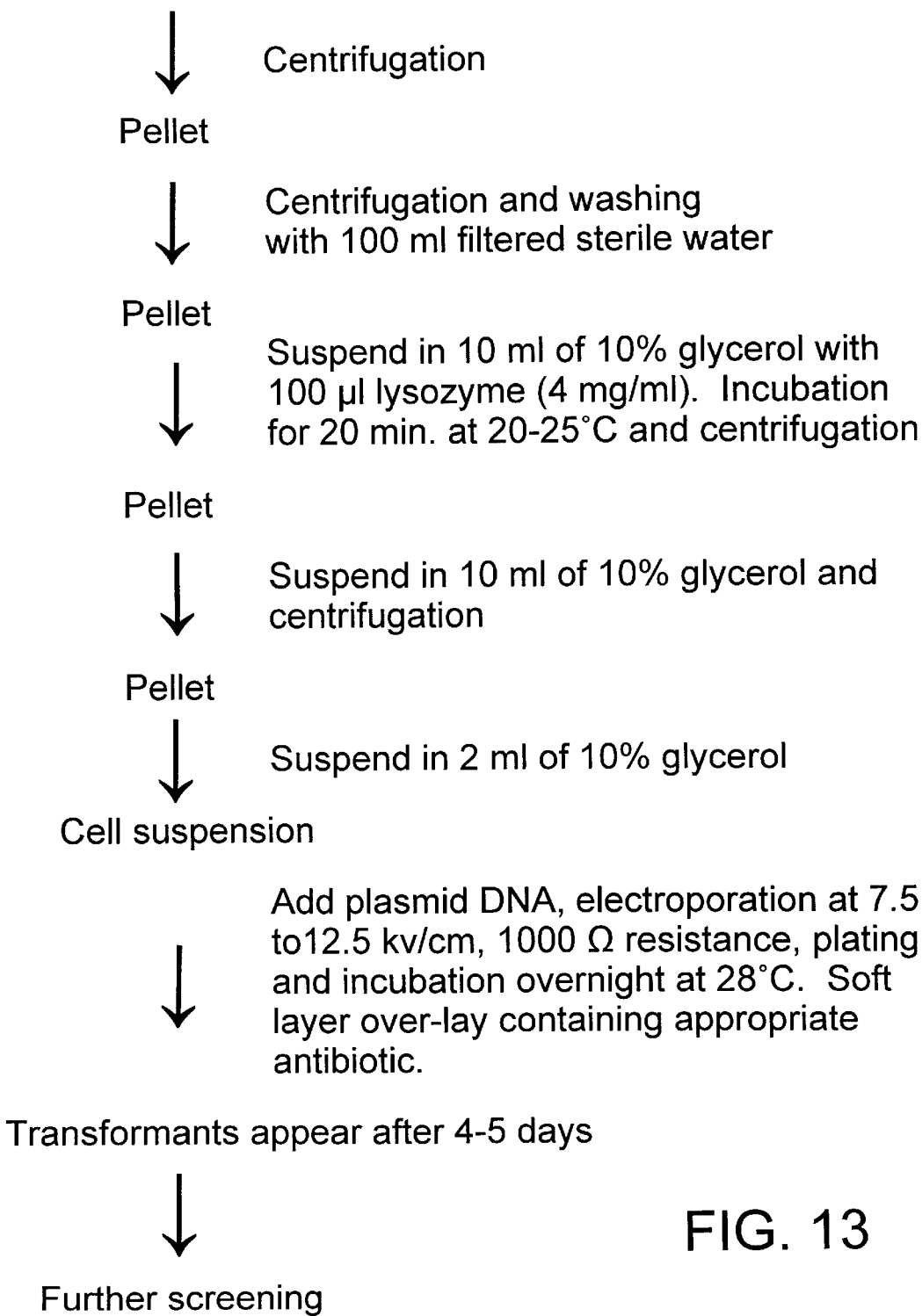
FIG. 13 shows the protocol for transformation through electroporation.

The development of these cloning vectors also led to the standardization and optimization of the only method of transformation through electroporation. The method of electroporation is developed for different strains of A. mediterranei and is depicted in FIG. 13. In this method late log phase culture of A. mediterranei is harvested, washed with millipore filtered water suspended in non-ionic buffer 10% glycerol containing 100 μl (4 mg/ml) lysozyme and incubated for 20 minutes at 20–25° C. The mycelia are then harvested by centrifugation at 3000 rpm for 15 mins., pellet washed with 10 ml 10% glycerol and suspended in 2–4 ml of 10% glycerol. 200 μl of this cell suspension was transferred to electroporation cuvettes (0.2 cm) and electroporated (by using BioRad Gene Pulser) at field strength 7.5–12 kV/cm, resistance 800–1000 Ω and capacitance 25 μF. Electroporated cells are plated on YM medium and incubated overnight. The YM agar plates are then overlaid with 2.5 ml of YM soft agar containing appropriate concentration of antibiotic. Under these transformation parameters a transformation efficiency nearly $1 \times 10^5$ transformants/μg DNA is obtained which is almost at par with that reported for Streptomyces lividans which is considered to be the E. coli of Gram positive bacteria. The development of these vectors and transformation method also provides the selection of suitable marker genes such as am, α-amy and ermE, which are expressed very well in A. mediterranei thus overcoming the problem of choice of suitable marker genes for these organisms.

The invention has now led to the development of series of effective cloning vectors (independent of Streptomyces cloning vectors) for the species of Amycolatopsis (Streptomyces cloning vectors and other cloning vectors found unsuitable for Amycolatopsis). This invention has also brought within the scope of recombinant DNA technology, several industrially important actinomycetes such as A. mediterranei DSM 40773 (rifamycin B); A. mediterranei DSM 43304 (Rifamycin SV); A. mediterranei DSM 46095 (rifamycin B); A. mediterranei DSM 46096 (rifamycin derivative); A. mediterranei MTCC 14 (rifamycin SV); A. mediterranei MTCC 17 (rifamycin SV); A. orientalis DSM 40040 (vanomycin); A. mediterranei W-2800 ans-12 (rifamycin W); A. mediterranei T-208 ans-11 pur-20 (rifamycin W and purine auxotroph); A. mediterranei 206 ans-13, leuc-1 str-2, (Protorifamycin, leucine auxotroph, streptomycin resistance); A. mediterranei F1/24 ans-13 (protorifamycin); A. mediterranei T-195, ans-13, thi-8 (Protorifamycin, thiamine auxotroph); A. mediterranei S2802 ans-4, his-3 (rifa S, histidine auxotroph); A. mediterranei S2804 ans-4 and ser 5 (rifa S serine auxotroph) (Table 1). These bacteria until recently were not accessible for recombinant DNA techniques. Thus these vectors can now be suitably used in the cloning, characterization and manipulation of genes involved in the synthesis of antibiotics, restriction enzyme and amylases, proteases or other useful products from these organisms.

In addition pRL60 can be used for direct cloning and selection of transformants by using α-amylase gene as a morphological marker. FIG. 14 depicts the salient features of pRL series. The major advantage of the cloning vector pRL60 containing α-amylase gene will be the use of α-amylase gene as the morphological marker for the selection of transformants and recombinants. Vectors of the pRL-series has a broad host range as they can be transformed almost in all species of Amycolatopsis and different strains of A. mediterranei so far tested (Table 1).

EXAMPLE I

Figure 1:
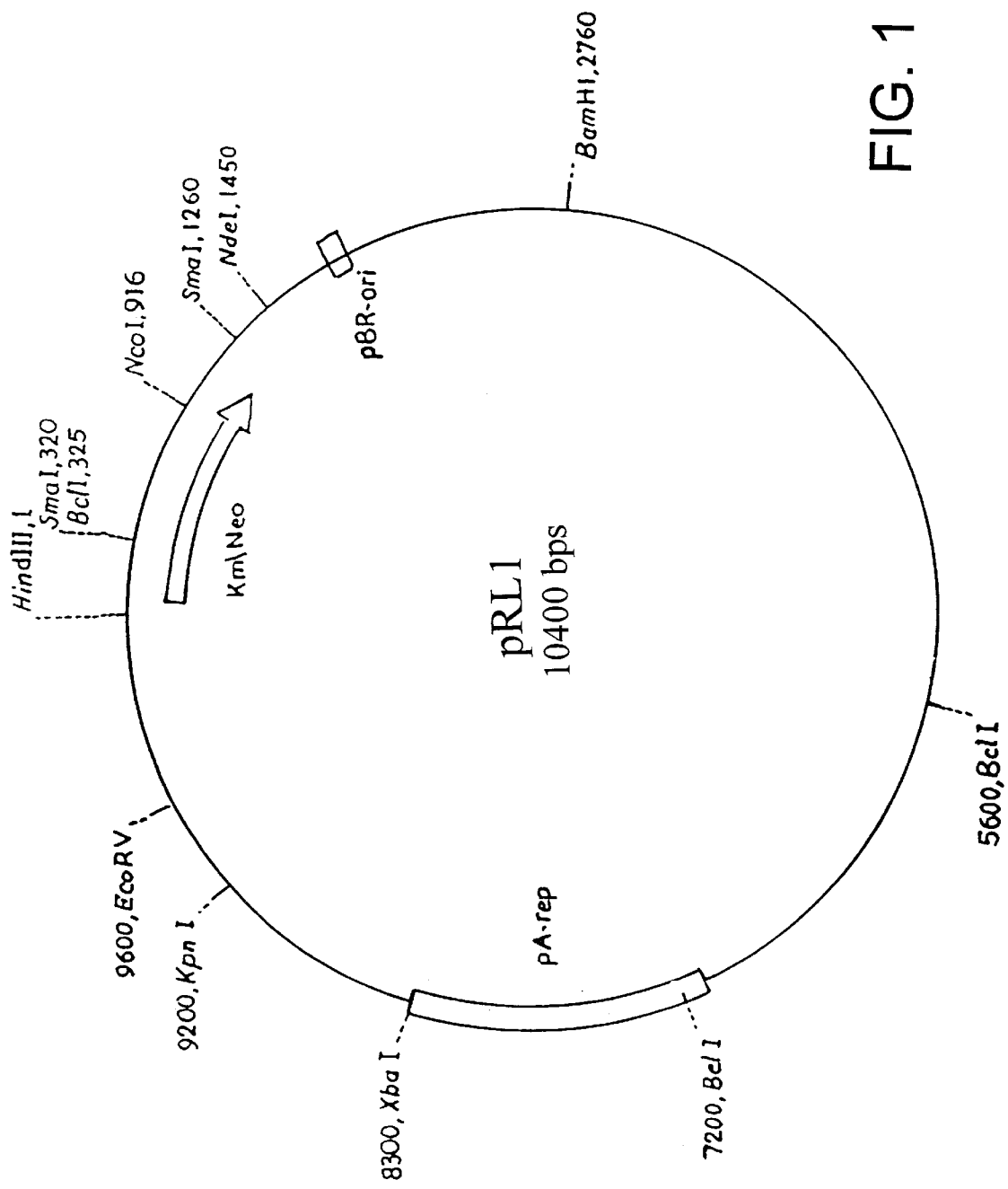
FIG. 1 shows the restriction map of preliminary cloning vector pRL1.
Figure 2A:
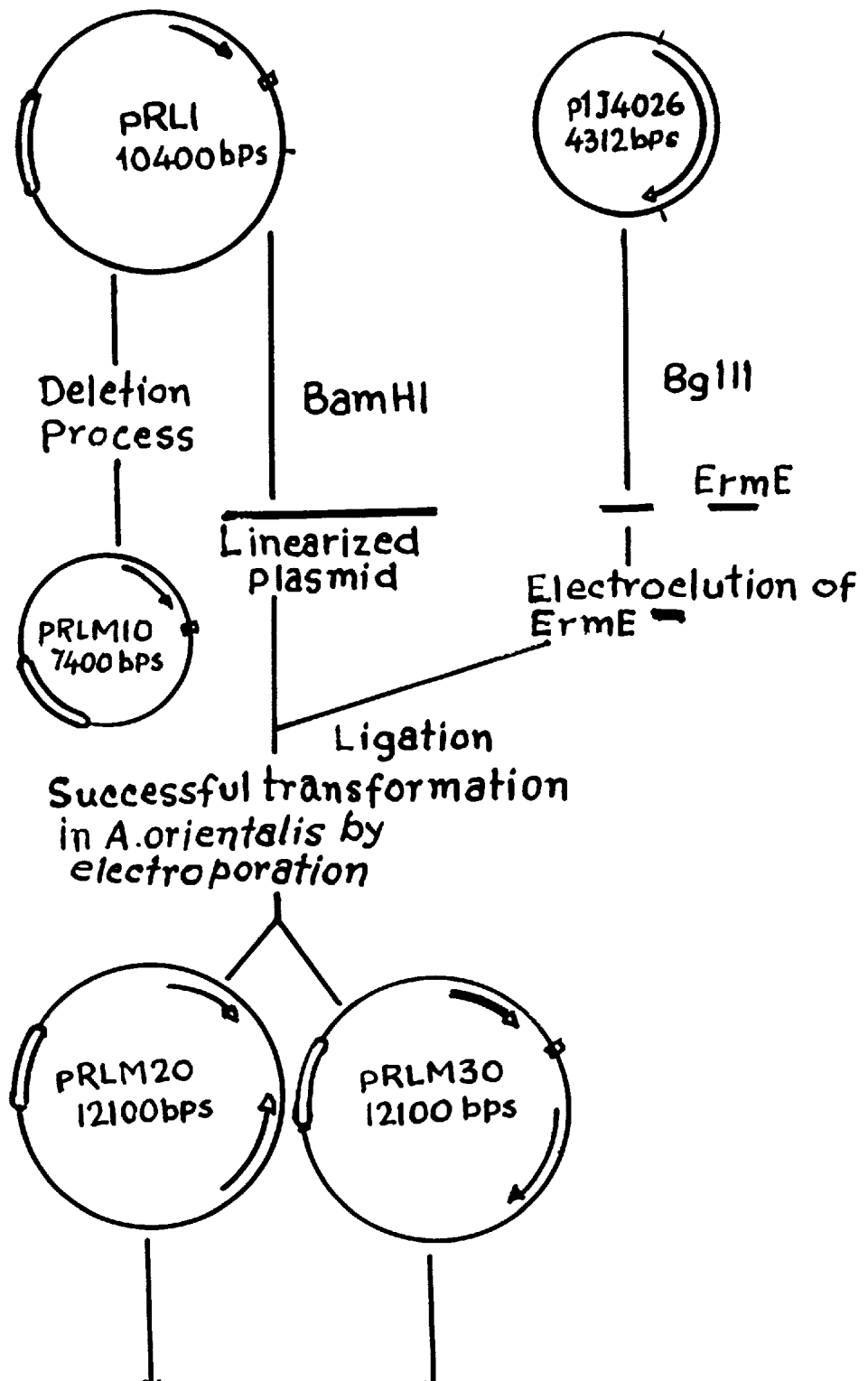
FIG. 2 shows the detailed process of the method for development of several cloning vectors of pRL1 in A. mediterranei. The process as explained, primarily requires the generation of unstable plasmid (concatamer) in E. coli and then transformation of these unstable plasmids in A. mediterranei through electroporation and selection of transformants under different antibiotic pressure. pA-rep is the replicon from pA387 of A. mediterranei DSM 43387 and ori-pBR is pBR-322 origin of replication kn/neo, ermE, and am are kanamycin/neomycin, erythromycin and apramycin resistance gene respectively. α-amy is α-amylase gene of S. griseus.
Figure 2B:
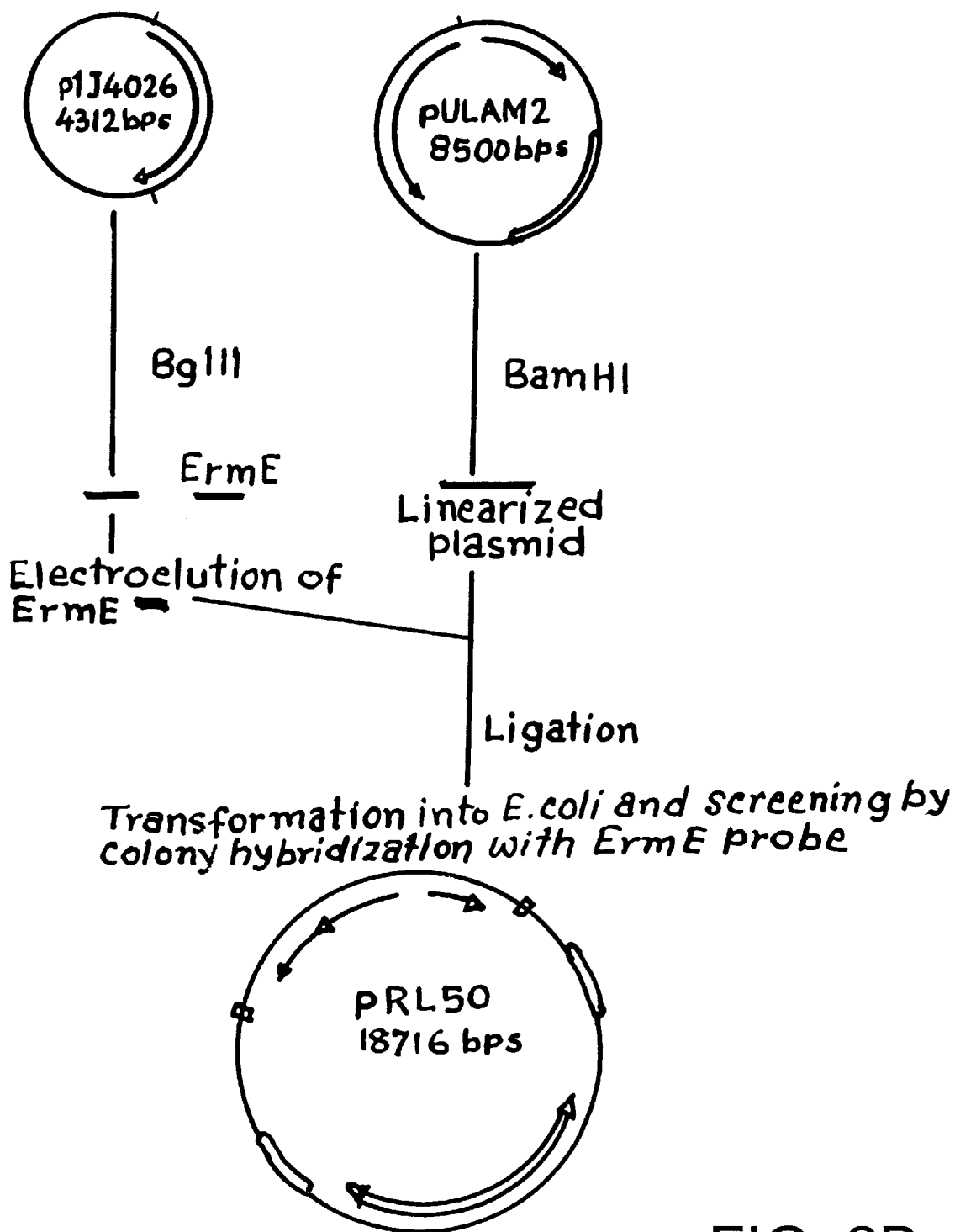
Figure 2E:
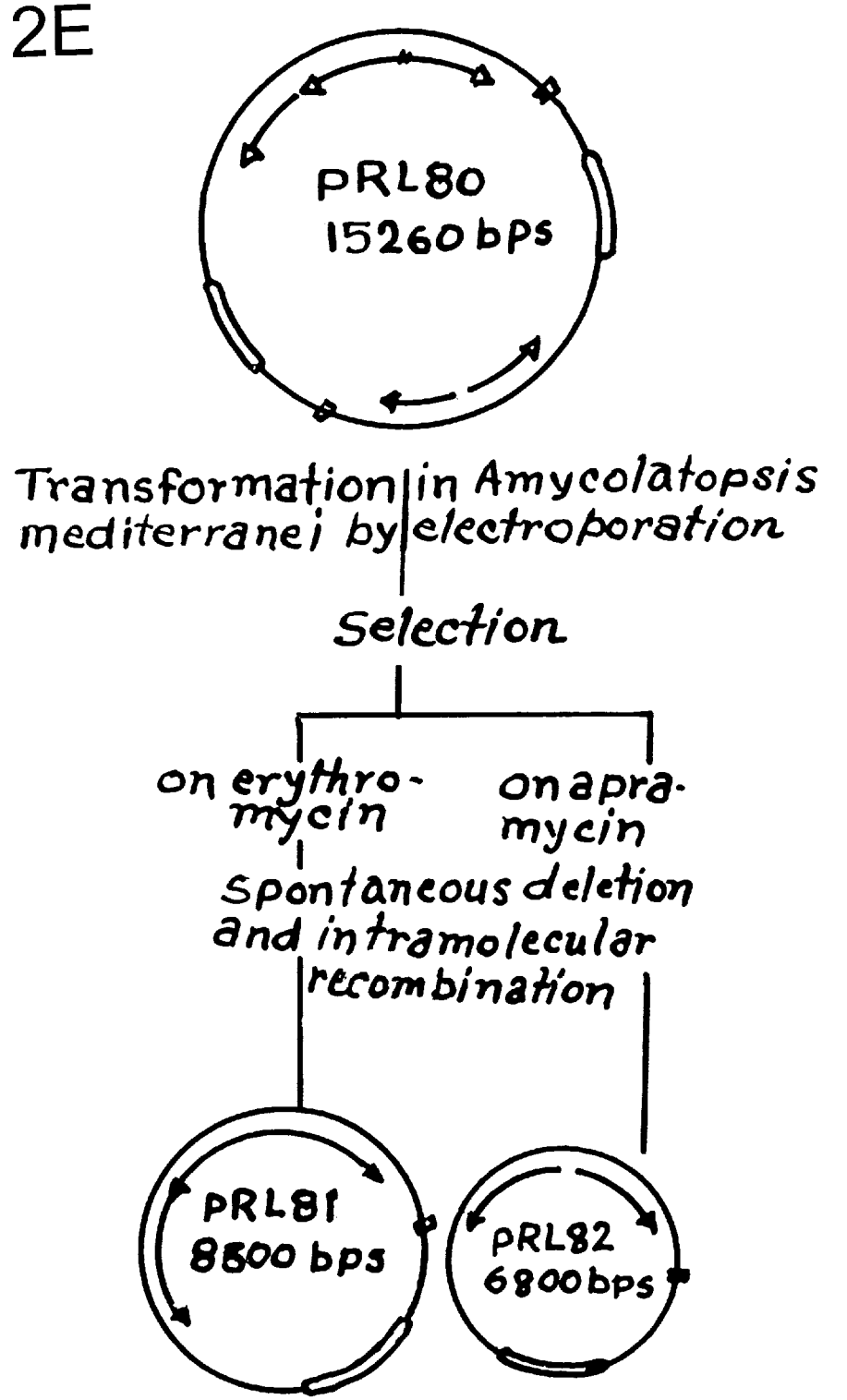

Thus a process for the development of cloning vectors for genetic manipulations of different species of Amycolatopsis has been developed. For this purpose all basic DNA manipulation such as plasmid isolation, restriction digestions agarose gel electrophoresis, ligation and E. coli transformation, southern blot hybridization and restriction mapping were performed by standard protocols described in (Sambrook et al. Molecular Cloning: A Laboratory Manual, 2nd Ed. Cold Spring Harbor Laboratory Press, Cold Spring Harbor, N.Y. 1989) (Hopwood et al. Laboratory Manual John Innes foundation Norwich 1985 and Lal et al. Appl. Environ. Microbiol. 57:, 665–671, 1991). In this process an antibiotic resistance gene ermE is cloned in pRL1 derivative km/neo, α-amylase or apramycin genes leading to the development of concatamers (pRL50 and pRL80). These concatamers when transformed in A. mediterranei and transformants selected under different antibiotic pressure to produce several effective cloning vectors (FIG. 2).

The process comprises selecting at first cloning vector pRL1 derivatives and digesting them with suitable restriction enzymes to make them linear, digesting a second cloning vector pIJ4026 containing ermE gene and isolating ermE gene, ligating the said ermE gene separately with the linearized DNA of pRL1 derivatives, transforming, selecting and isolating recombinant plasmids containing ermE inserts in E. coli. The concatamers say pRL50 or pRL80 containing ermE inserts are then transformed into A. mediterranei for intramolecular recombinations.

The approach described here involves two steps (1) introduction of an additional copy of the cloning vector alongwith ermE into a derivative of pRL1, thus constructing a large sized unstable plasmid vector first in E. coli, and (ii) transforming this unstable vector into A. mediterranei, and then antibiotic selection pressure is used as regulator for deletions and intramolecular recombination. Thus this technology has been used not only in reducing the size of the vector through intramolecular recombinations but also becomes a model to demonstrate the generation of deletions and recombinations in A. mediterranei (FIG. 2).

EXAMPLE II

The development of effective cloning vectors has led to the development of a protocol for electrotransformation in A. mediterranei which is outlined in FIG. 13. In this, method stationary phase culture of A. mediterranei is taken, harvested by centrifugation and washed in millipore filtered water. The pellet is suspended in 10 ml 10% glycerol containing 100 μl of lysozyme solution (4 mg/ml) and mycelia incubated for 20 mins. at 25° C. These cells are pelleted, washed with 10% glycerol and pellet suspended in appropriate quantities of 10% glycerol. The mycelia (200 ul) suspension is then pulsed at field strength 7.5 to 12.5 kV/cm, resistance 1000 Ω and capacitance 25 μF and transformants are selected under different antibiotic pressure. This method as mentioned earlier resulted in transformation efficiency of nearly $1 \times 10^5$ transformants/ug DNA.

EXAMPLE III

The final selection of selectable markers (among several marker genes which are now available for actinomycetes) for *A. mediterranei* has been made. The markers which functions effectively in *A. mediterranei* are ermE, α-amy and am. Apart from the use of ermE, am and km/neo, for the selection of transformants, α-amy which excretes α-amylase extracellularly was used as a morphological marker. For this purpose transformants containing plasmid with α-amylase gene are grown on a medium containing 1% starch. When sufficient growth is achieved, the plates are sprayed with iodine vapors. A halo around the transformants confirms α-amylase activity. This is shown in FIG. 14. The methodology will also be useful in future studies aimed at developing cloning vectors with appropriate markers and with appreciable reduction in size bypassing the process of creating deletions through restriction enzymes and exonucleases.

TABLE 1

HOST RANGE OF pRL1-SERIES OF CLONING VECTORS

| Organisms | Strain | Characteristic |
| --- | --- | --- |
| A. mediterranei | *DSM 40773 | Rifamycin B |
| A. mediterranei | DSM 43304 | Rifamycin SV |
| A. mediterranei | DSM 46095 | Rifamycin SV |
| A. mediteranei | DSM 46096 | Rifamycin derivatives |
| A. mediterranei | **MTCC 14 | Rifamycin B |
| A. mediterranei | MTCC-17 | Rifamycin SV |
| A. mediterranei | W-2800 ans-12 | Rifamycin W |
| A. mediterranei | T-208 ans-11 pur-20 | Rifamycin W (purine auxotroph) |
| A. mediterranei | T-206 ans-13 leu-1 str.2 | Protorifamycin (leucine auxotroph, streptomycin resistance) |
| A. mediterranei | F$_1$/24 ans-13 | Protorifamycin |
| A. mediterranei | T-195 ans-13, thi-8 | Protorifamycin (thiamine auxotroph) |
| A. mediterranei | S2802 ans-4, his-3 | Rifa S (histidine auxotroph) |
| A. mediterranei | S2804 ans-4 ser-5 | Rifa S (serine auxotroph) |
| A. orientalis | DSM 40040 | Vancomycin |

*DSM:Deutsche Sammlung von Mikroorganismen und Zellkulturen GmbH Braunschweig, Germany.
**MTCC:Microbial Type Culture Collection, Chandigarh, India.

I claim:

1. The concatamer designated pRL50 of 18.7 kb, said concatamer comprising two copies each of km/neo, α-amy, pA-rep, and pBR-ori, and one copy of ermE.

2. The cloning vector designated pRL60 of 10.2 kb, said cloning vector comprising km/neo, ermE, α-amy, pA-rep, and pBR-ori.

3. The concatamer designated pRL80 of 15.2 kb, said concatamer comprising two copies each of km/neo, pA-rep, am, and pBR-ori, and one copy of ermE.

4. The cloning vector designated pRL81 of 8.5 kb, said cloning vector comprising am, km/neo, ermE, pA-rep, and pBR-ori.

5. The cloning vector designated pRL82 of 6.8 kb, said cloning vector comprising am, km/neo, pA-rep, and pBR-ori.

6. The cloning vector designated pRL51 of 5.0 kb, said cloning vector comprising km/neo, pA-rep, and pBR-ori.

7. The cloning vector designated pRL53 of 7.1 kb, said cloning vector comprising km/neo, ermE, pA-rep, and pBR-ori.

8. A method for the preparation of concatamer pRL50 comprising the steps of:

(i) inserting into plasmid pULAM2 a DNA molecule comprising an ermE gene that is expressed in cells of Amycolatopsis species to confer resistance to erythromycin;

(ii) introducing the modified plasmid into *E. coli*, screening the transformants, identifying the transformants containing concatamer, and isolating and analyzing the concatamers to obtain pRL50.

9. A method for the preparation of concatamer pRL80 comprising the steps of:

(i) inserting into plasmid pULVK2A a DNA molecule comprising an ermE gene that is expressed in cells of Amycolatopsis species to confer resistance to erythromycin;

(ii) introducing the modified plasmid into *E. coli*, screening the transformants, identifying the transformants containing concatamers, and isolating and analyzing the concatamers to obtain pRL80.

10. A method for the preparation of a cloning vector that operates in cells of an Amycolatopsis species, comprising the steps of:

(i) inserting into a plasmid comprising an origin of replication that functions in cells of an Amycolatopsis species at least one DNA molecule selected from the group consisting of:
an ermE gene that is expressed in cells of Amycolatopsis species to confer resistance to erythromycin,
a km/neo gene that is expressed in cells of Amycolatopsis species to confer resistance to neomycin, and
an am gene that is expressed in cells of Amycolatopsis species to confer resistance to apramycin, (ii) introducing said modified plasmid into *E. coli*, screening the transformants, identifying the transformants containing concatamers, and isolating the concatamers;

(iii) introducing the concatamers into cells of an Amycolatopsis species and growing the transformants in the presence of erythromycin, neomycin, or apramycin, which antibiotic is one to which the cells have been transformed to be resistant, and (iv) screening the cells that grow in the presence of the antibiotic, identifying transformants containing said cloning vector, wherein said cloning vector comprises fewer nucleotides than the concatamer with which said cells were transformed, and isolating said cloning vector.

11. The method of claim 10 wherein said concatamers are introduced into said cells of an Amycolatopsis species by electroporation.

12. A method for introducing DNA into cells of an Amycolatopsis species, comprising:

(i) culturing cells of an Amycolatopsis species to obtain stationary phase mycelial cells, and harvesting the cells by centrifugation;

(ii) suspending the mycelial pellet in glycerol containing lysozyme, incubating, harvesting the mycelia by centrifugation, and suspending the mycelia in aqueous solution comprising glycerol;

(iii) mixing the mycelia with the DNA to be introduced, and pulsing the cell suspension at field strength of 7.5–12.5 kV/cm.

13. A method for obtaining expression of a gene in cells of an Amycolatopsis species, comprising:

(i) inserting into a plasmid comprising an origin of replication that functions in cells of an Amycolatopsis species at least one DNA molecule selected from the group consisting of:

an ermE gene that is expressed in cells of Amycolatopsis species to confer resistance to erythromycin, a km/neo gene that is expressed in cells of Amycolatopsis species to confer resistance to neomycin, and an am gene that is expressed in cells of Amycolatopsis species to confer resistance to apramycin, (ii) introducing the modified plasmid into *E. coli*, screening the transformants, identifying the transformants containing concatamers, and isolating the concatamers;

(iii) introducing the concatamers into cells of an Amycolatopsis species and growing the transformants in the presence of erythromycin, neomycin, or apramycin, which antibiotic is one to which the cells have been transformed to be resistant, (iv) screening the cells that grow in the presence of the antibiotic, identifying transformants containing a cloning vector, said cloning vector comprising fewer nucleotides than the concatamer with which said cells were transformed, and isolating said cloning vector;

(v) inserting into said cloning vector a DNA molecule comprising the gene to be expressed in cells of an Amycolatopsis species, which gene is operably linked to DNA transcription regulatory elements which direct transcription in cells of an Amycolatopsis species; and (vi) introducing said cloning vector comprising the gene to be expressed into cells of an Amycolatopsis species, so that said gene is expressed in said cells.

14. The method of claim 13, wherein said gene to be expressed is inserted into a cloning vector selected from the group consisting of pRL51, pRL53, pRL60, pRL81, and pRL82; and said cloning vector comprising said gene is then introduced into cells of an Amycolatopsis species so that said gene is expressed in said cells.

15. The method of claim 13, wherein said cloning vector is introduced into Amycolatopsis cells which are selected from the group consisting of:

*A. mediterranei* DSM 40773, (rifamycin B);

*A. mediterranei* 43304 (rifamycin B);

*A. mediterranei* 46095 (rifamycin SV);

*A. mediterranei* 46096 (rifamycin derivatives);

*A. mediterranei* MTCC 14 (rifamycin B);

*A. mediterranei* MTCC 17 (rifamycin SV);

*A. mediterranei* W-2800, ans-12 (rifamycin W);

*A. mediterranei* T-208, ans-11 pur-20 (rifamycin W and purine auxotroph);

*A. mediterranei* T-206, ans-13, leuc-1, str. 2 (protorifamycins, leucine auxotroph, streptomycin resistance);

*A. mediterranei* F1/24, ans-13 (protorifamycin);

*A. mediterranei* T-195, ans-13, thi-8 (protorifamycin, thiamine auxotroph);

*A. mediterranei* S2802, ans-4, his-3 (rifa S, histidine auxotroph);

*A. mediterranei* S2804, ans-4, ser-5 (rifa S, serine auxotroph); and

*A. orientalis* DSM 40040 (vancomycin).

16. A method for the preparation of cloning vector pRL51 comprising:

(a) introducing pRL50 into *A. mediterranei* cells;

(b) growing the transformants in the presence of neomycin to obtain cells containing cloning vector pRL51; and (c) isolating cloning vector pRL51 from said cells containing pRL51.

17. A method for the preparation of cloning vector pRL60 comprising:

(a) introducing pRL50 into *A. mediterranei* cells;

(b) growing the transformants in the presence of erythromycin to obtain cells containing cloning vector pRL60; and (c) isolating cloning vector pRL60 from said cells containing pRL60.

18. A method for the preparation of cloning vector pRL81 comprising:

(a) introducing pRL80 into *A. mediterranei* cells;

(b) growing the transformants in the presence of erythromycin to obtain cells containing cloning vector pRL81; and (c) isolating cloning vector pRL81 from said cells containing pRL81.

19. A method for the preparation of cloning vector pRL82 comprising:

(a) introducing pRL80 into *A. mediterranei* cells;

(b) growing the transformants in the presence of apramycin to obtain cells containing cloning vector pRL82; and (c) isolating cloning vector pRL82 from said cells containing pRL82.

\* \* \* \* \*